(12) United States Patent
Mehus et al.

(10) Patent No.: US 8,012,421 B2
(45) Date of Patent: Sep. 6, 2011

(54) CONCENTRATION MONITOR

(75) Inventors: Richard J. Mehus, Richfield, MN (US); Charles A. Hodge, Cottage Grove, MN (US); Quang Van Dao, Eden Prairie, MN (US)

(73) Assignee: Ecolab Inc., St. Paul, MA (US)

( * ) Notice: Subject to any disclaimer, the term of this patent is extended or adjusted under 35 U.S.C. 154(b) by 1937 days.

(21) Appl. No.: 10/602,384

(22) Filed: Jun. 24, 2003

(65) Prior Publication Data

US 2004/0265174 A1 Dec. 30, 2004

(51) Int. Cl.
*G01N 33/00* (2006.01)
(52) U.S. Cl. .............. 422/82.02; 422/50; 422/82.01; 436/149; 436/150
(58) Field of Classification Search .......... 73/1.02, 73/53.01, 1.01; 422/82.01, 82.02, 50, 68.1; 436/43, 149, 150
See application file for complete search history.

(56) References Cited

U.S. PATENT DOCUMENTS

| | | | | |
|---|---|---|---|---|
| 1,472,125 | A | * | 10/1923 | Keeler ............... 324/443 |
| 2,224,382 | A | * | 12/1940 | Douty ............... 324/439 |
| 3,399,037 | A | * | 8/1968 | Eckfeldt ............ 205/778.5 |
| 3,831,083 | A | * | 8/1974 | Teass et al. ......... 324/444 |
| 4,076,146 | A | | 2/1978 | Lausberg et al. |
| 4,204,259 | A | * | 5/1980 | Yabe ................ 702/25 |
| 4,266,188 | A | * | 5/1981 | Thompson ........... 324/649 |
| 4,469,146 | A | * | 9/1984 | Campbell et al. ...... 141/9 |
| 4,486,910 | A | | 12/1984 | Saalmann et al. |
| 4,733,798 | A | | 3/1988 | Brady et al. |
| 4,964,185 | A | | 10/1990 | Lehn |
| 5,370,743 | A | | 12/1994 | Usui et al. |
| 5,390,385 | A | | 2/1995 | Beldham |
| 5,500,050 | A | | 3/1996 | Chan et al. |

(Continued)

FOREIGN PATENT DOCUMENTS

DE 198 52 164 A1 5/2000

OTHER PUBLICATIONS

"About Conductivity", Great Lakes Instruments, 1 page.

*Primary Examiner* — Sam P Siefke
(74) *Attorney, Agent, or Firm* — Shumaker & Sieffert P.A.

(57) ABSTRACT

A concentration monitor for monitoring a concentration of a plurality of use solutions, each of the plurality of use solutions being, at least, a concentrate in a diluent, each of the plurality of use solutions having a resistivity which varies as a function of both temperature and an amount of the concentrate contained in a given amount of the diluent. A resistivity probe is adapted for use with at least one of the plurality of use solutions for taking a measurement related to the resistivity of the at least one of the plurality of use solutions. A temperature sensor is adapted for use with the at least one of the plurality of use solutions for taking a measurement related to the temperature of the at least one of the plurality of use solutions. A controller calculates the concentration of the at least one of the plurality of the use solutions based upon a predetermined algorithm using the resistivity and the temperature for the particular one of the at least one of the plurality of use solutions, the algorithm being based upon knowledge of the at least one of the plurality of use solutions being measured.

13 Claims, 7 Drawing Sheets

U.S. PATENT DOCUMENTS

| | | |
|---|---|---|
| H1743 H | 8/1998 | Graves et al. |
| 5,913,915 A | 6/1999 | McQuinn |
| 5,979,703 A | 11/1999 | Nystrom |
| 5,987,105 A | 11/1999 | Jenkins et al. |
| 6,012,041 A | 1/2000 | Brewer et al. |
| 6,259,956 B1 | 7/2001 | Myers et al. |
| 6,706,533 B2 * | 3/2004 | Nomura et al. ............... 436/150 |
| 6,792,395 B2 | 9/2004 | Roberts |
| 7,069,188 B2 | 6/2006 | Roberts |
| 2002/0142935 A1 | 10/2002 | Oubrahim et al. |

* cited by examiner

CONCENTRATION MONITOR

TECHNICAL FIELD

This invention relates to liquid concentration monitors and, in particular, to liquid concentration monitors utilizing conductivity measurements.

BACKGROUND

Certain washers use a solution, known as a use solution or a working solution, consisting mainly of concentrate, e.g., detergent, and a diluent, e.g., water. As the use solution is utilized and the effects of the detergent concentrate are gradually diminished, the use solution becomes less concentrated and the use solution becomes less effective. At an appropriate time, either the use solution must be changed or additional concentrate must be added to increase the concentration of the concentrate, e.g., detergent, in the use solution to bring the concentration of concentrate in the use solution to within an acceptable range. A user of such a use solution must keep track of the concentration of the use so as to know when to add concentrate to the use solution and how much concentrate to add to the use solution.

Concentration monitors are typically used for this purpose. Concentration monitors determine the amount, for example, on a percentage basis, of concentrate contained in a known use solution. Electrical characteristics of some use solutions vary as a function of the concentration. For example, if a concentrate is more electrically conductive than a diluent, then the conductivity of the use solution will increase as the percentage amount of concentrate is increased in the use solution. Thus, a concentration monitor that could sense the conductivity of the use solution could determine that concentrate needed to be added to the use solution when the conductivity of the use solution dropped to a pre-determined level. A concentration monitor of this type could either, for example, automatically add concentrate to the use solution or, alternatively, could report the concentration level, or sound an alarm, and let the user determine the appropriate course of action to be taken.

Conductivity type concentration monitors typically use a particular cell, a probe for insertion into the use solution, for a particular product concentrate, or class of product concentrate, being monitored. Different use solutions, particularly different types of use solutions for different product classes, e.g., different types of detergents such phosphate and non-phosphate detergents, have different cell constants. A cell constant is the surface area of the conductive agent in the use solution which is exposed to the cell, or probe, monitoring the concentration. A particular cell, or probe, is selected for a use solution containing a particular product, or product class, depending on the cell constant of the use solution.

Newer generations of detergent products, e.g., extruded detergents, have naturally low conductivity. Thus, the cell constant is markedly different for these types of newer detergents as compared with traditional detergents.

Therefore, existing concentration monitors with existing cells, probes, which were designed for traditional detergents, won't work properly with the newer generations of detergents. This requires swapping out a multiplicity of probes in a multiplicity of existing installations with new probes compatible with newer generations of detergent. With a large number of existing installations, swapping out existing probes for new probes would be very costly and time consuming as well as disruptive to existing installations.

In addition, the same probe would not work for both classes of detergent product. This would require the customer (user) to have multiple probes in stock and to actually change probes when a different detergent product, or class of detergent products, is used. The customer would have to insert a different probe whenever a detergent product was changed or a class of detergent products was changed in order to use the proper cell, probe, for the current detergent product, or class of detergent products, being used.

SUMMARY OF THE INVENTION

Thus, there is a need to expand the usefulness of conductivity type concentration monitors. The concentration monitor should be useful over a variety of products and product classes, not only detergents but also cleaners used, for example, in vehicle care, pool & spa environments, and in typical higher strength formulations typically found in food & beverage applications.

A solution is a concentration monitor which can use a single cell, probe, for measuring the conductivity of a wider range of products, or classes of products, over a wide range of concentrations and a wide range of temperatures. A controller in the concentration monitor calculates the concentration of the use solution based upon a measured resistivity (or conductivity) and a measured temperature in accordance with a predetermined algorithm for a particular use solution, i.e., for a use solution having a particular concentrate, or a particular class of concentrates. Such a concentration monitor is useful over a variety of use solutions having a variety of conductivities and is useful over a variety of temperature ranges.

The problem of swapping out cells, probes, whenever the particular concentrate or type of use solution is changed is eliminated. The existing cell, or probe, may be used on a variety of use solutions by changing the algorithm used by the controller in the concentration monitor. Thus, the customer may use existing probes on a new detergent concentrate, for example. The customer doesn't have to switch probes when switching to a different use solution or a different type of use solution.

A plurality of algorithms may be stored in the controller. A user may then select a particular algorithm which is useful with the particular use solution being utilized or about to be utilized. Thus, the concentration monitor can be adapted for a different type of use solution by selecting an appropriate algorithm. The user could select the appropriate algorithm during set up of the concentration monitor at the time that a different use solution is prepared. Selecting an appropriate algorithm is much easier, more cost effective and less obtrusive than swapping out cells, probes. Further, different types of probes would not need to be stocked for different concentrate products or types of concentrate products. This would enable a user to easily switch back and forth between different concentrate products or classes of concentrate products, if desired.

In one embodiment, the present invention provides a concentration monitor for monitoring a concentration of a plurality of use solutions. Each of the plurality of use solutions consists of, at least, a concentrate in a diluent, and each of the plurality of use solutions has a resistivity which varies as a function of both temperature and an amount of the concentrate contained in a given amount of the diluent. A resistivity probe is adapted for use with at least one of the plurality of use solutions for taking a measurement related to the resistivity of the at least one of the plurality of use solutions. A temperature sensor is adapted for use with the at least one of the plurality of use solutions for taking a measurement related to the temperature of the at least one of the plurality of use solutions. A controller, operatively coupled to the resistivity probe and the temperature sensor, calculates the concentration of the at least one of the plurality of the use solutions based upon a predetermined algorithm using the resistivity and the temperature for the particular one of the at least one of the plurality of use solutions, the algorithm being based upon knowledge of the at least one of the plurality of use solutions being measured.

In a preferred embodiment, the controller stores the knowledge of which of the at least one of the plurality of use solutions are being measured.

In another embodiment, the present invention provides, a concentration monitor for monitoring a concentration of a use solution, the use solution consisting of, at least, a concentrate in a diluent, and which has a resistivity which varies as a function of both temperature and an amount of the concentrate contained in a given amount of the diluent. A resistivity probe is adapted for use with the use solution for taking a measurement related to the resistivity of the use solution. A temperature sensor is adapted for use with the use solution for taking a measurement related to the temperature of the use solution. A controller is operatively coupled to the resistivity probe and the temperature sensor. The controller stores an identification of which particular the use solution is being monitored and calculates the concentration of the use solution based upon a predetermined algorithm using the resistivity and the temperature for the use solution, the algorithm being based upon the identification of the use solution being measured.

In a preferred embodiment, the storing of the identification is accomplished, at least in part, by a user controllable setting.

In a preferred embodiment, the controller also reports the concentration to a user.

In a preferred embodiment, the controller performs a function based upon the concentration.

In a preferred embodiment, the function adds concentrate to the diluent when the concentration falls below a certain level.

In an alternative embodiment, the present invention provides a method of monitoring a concentration of a plurality of use solutions. Each of the plurality of use solutions being, at least, a concentrate in a diluent, each of the plurality of use solutions having a resistivity which varies as a function of both temperature and an amount of the concentrate contained in a given amount of the diluent. A resistivity probe is adapted for use with at least one of the plurality of use solutions for taking a measurement related to the resistivity of the at least one of the plurality of use solutions. A temperature sensor is adapted for use with the at least one of the plurality of use solutions for taking a measurement related to the temperature of the at least one of the plurality of use solutions. The particular one of the plurality of user solution from the plurality of use solutions is selected. The resistivity of the selected use solution is measured using the resistivity probe. The temperature of the selected use solution is measured using the temperature probe. The concentration of the selected use solution is calculated based upon a predetermined algorithm using the resistivity and the temperature for the particular one of the at least one of the plurality of use solutions, the algorithm being based upon which of the plurality of use solutions has been selected.

In a preferred embodiment, the method further reports the concentration to a user.

In a preferred embodiment the method further adds concentrate to the diluent when the concentration falls below a predetermined level.

In an alternative embodiment, the method further comprises inserting the resistivity probe and the temperature probe into the use solution.

DETAILED DESCRIPTION

The present invention describes a concentration monitor and method of use adapted for use with a use solution having a concentrate in a diluent. An example of a use solution for which the present invention is useful is a working washing solution consisting of a detergent diluted in water. A particular concentrate, or detergent, for example, or a particular class of concentrates, has its own use characteristics.

Each product or class of products, a product class, has different formulary chemistry and may have a different conductivity curve, especially when measured from very low to very high concentrations. Using detergent as an example, more caustic products, or product classes, tend to have higher conductivity relative to less caustic detergents.

In order to determine the actual concentration of a use solution, it is necessary to know the conductivity of the use solution at different levels of concentration over a range of temperatures. This may be done empirically by taking conductivity measurements at different product concentrations at different temperatures.

Conductivity can be measured by techniques and equipment well known in the art. As an example, conductivity may be measured by direct conductivity sensors or toroidal coils using an indirect inductive measurement. Typical sensing units range from zero to ten volts direct current or from 4 to 20 milliamperes depending on the sensor used.

Similarly, temperature can be directly measured by techniques and equipment well known in the art. As an example, a thermocouple or resistance temperature detector can be used.

Figure 1:
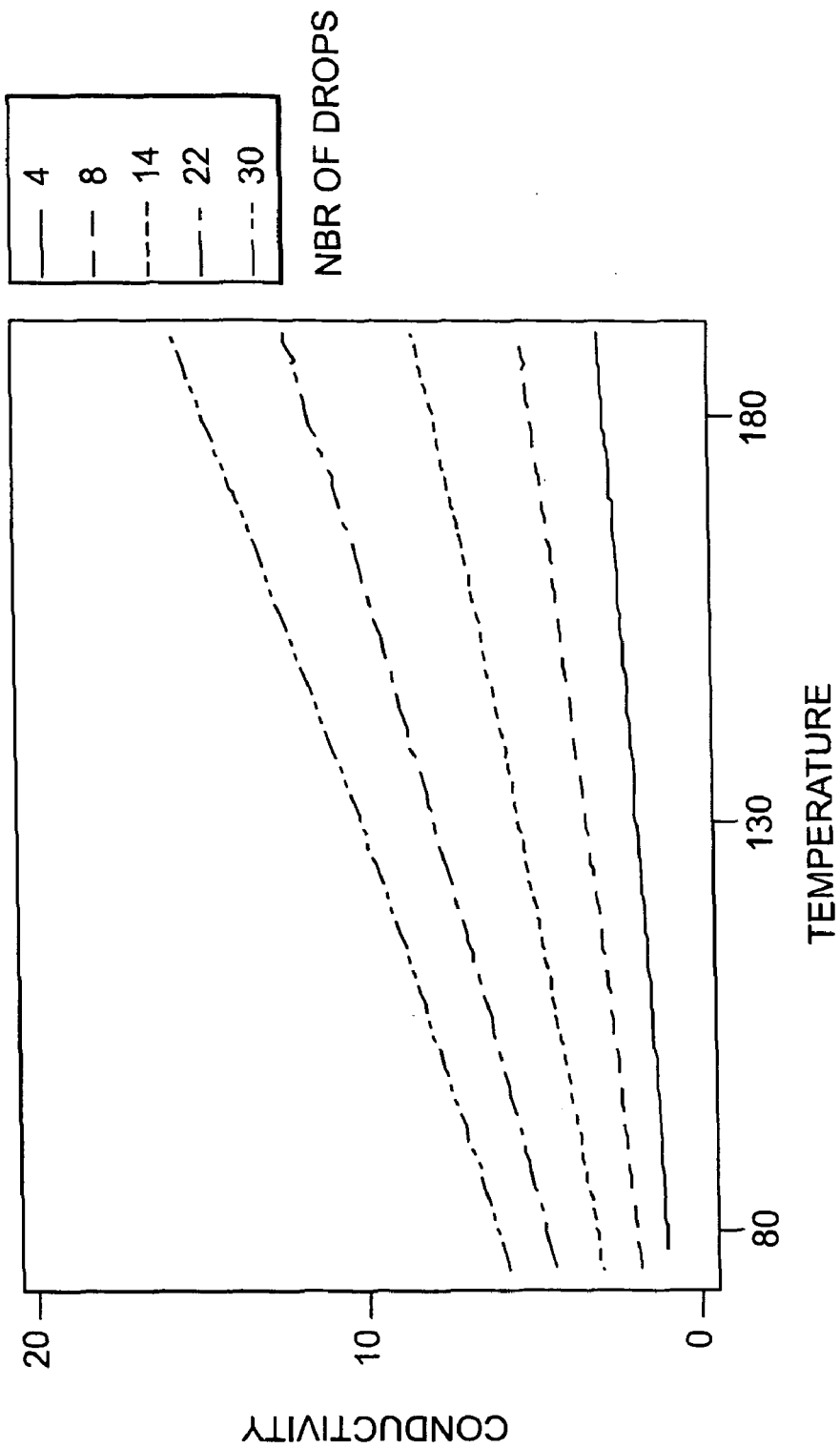
FIG. 1 is a chart illustrating the effect of both temperature and concentration on the conductivity of a particular use solution.

The chart of FIG. 1 illustrates the effect of both temperature and concentration on the conductivity of a particular use solution. The particular use solution illustrated is Kiseki NP (solid extruded detergent, non-caustic, non-phosphate (NTA) based on carbonate) in water. The ordinate in the chart is temperature in degrees Fahrenheit and the mantissa is conductivity in milliSiemens. A separate curve is shown for concentrations resulting from various numbers of drops on Kiseki NP concentrate in four (4) liters of water. For each concentration, the conductivity increases as the temperature increases. At a given temperature, the conductivity increases as the concentration increases as can be seen among curves at a given temperature. The spread of conductivity as a function of concentration at the lower temperature range is smaller than the range of conductivity as a function of concentration at the higher temperature range. Note that the conductivity curve for each amount of concentration is nearly linear.

Figure 2:
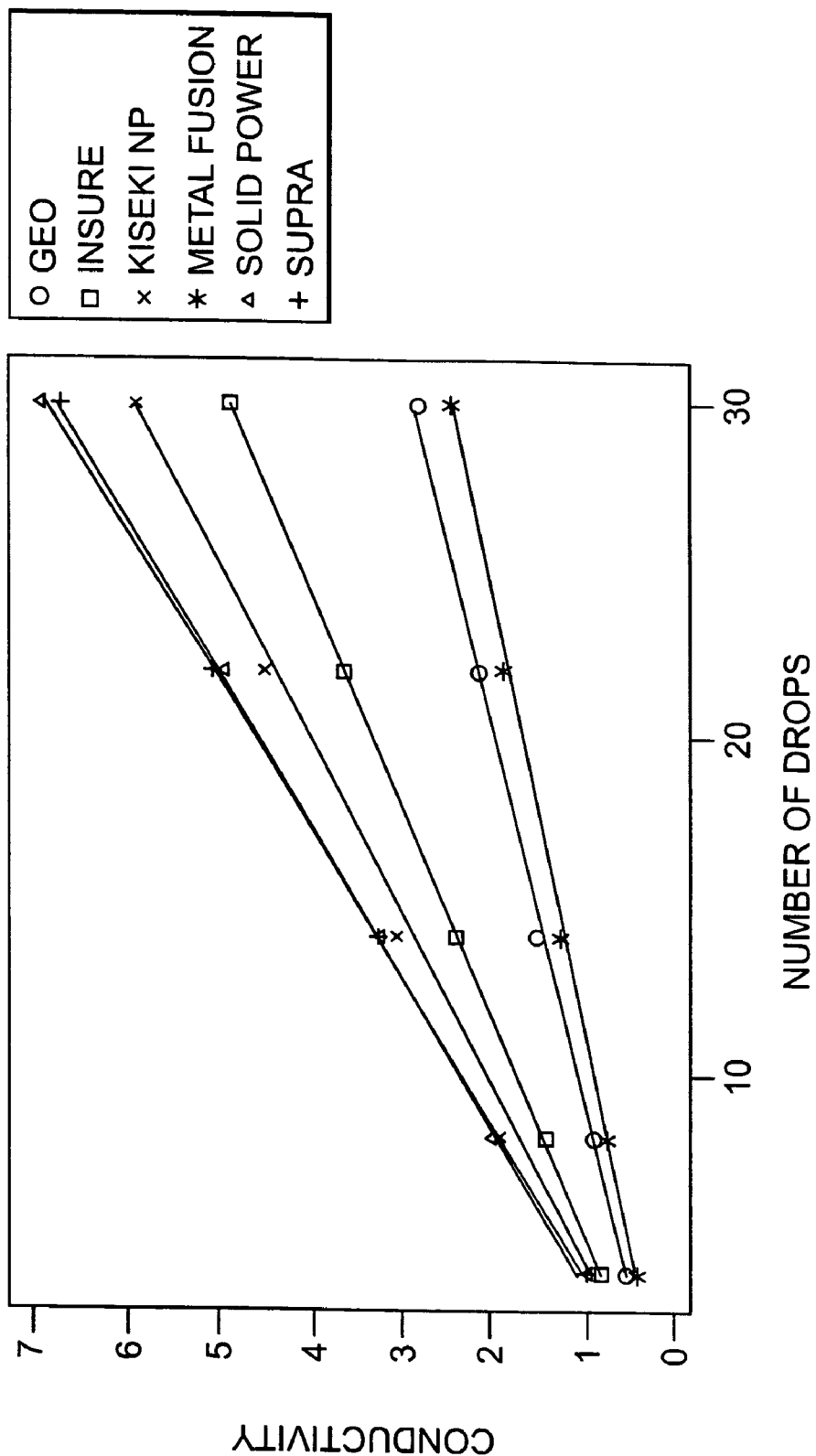
FIG. 2 is a chart illustrating the difference in conductivity of different detergents diluted in water at a particular temperature, in this case seventy-seven degrees (77°) Fahrenheit.

The chart of FIG. 2 illustrates the dramatic difference in conductivity of different detergents diluted in water at a particular temperature, in this case seventy-seven degrees (77°) Fahrenheit. The ordinate in the chart is the number of drops of concentrate added to four (4) liters of water. The mantissa is conductivity measured in milliSiemens. Each curve in the chart illustrates the change in conductivity which occurs as the concentration of the concentrate is increased. The conductivity curves for Geo Fusion (solid extruded detergent, non-caustic, phosphate based on carbonate) and Metal Fusion (solid extruded detergent, non-caustic, phosphate based on carbonate and silicate, metal protecting) have the lowest conductivities and the curves are very similar. The conductivity curves for Solid Power (solid cast caustic and phosphate) and Supra (solid cast caustic, non-phosphate NTA) have the highest conductivities and the curves are very similar. The conductivity curves for Insure (solid cast caustic, silicate based, non-phosphate NTA, metal protecting) and Kiseki NP have conductivities which are intermediate.

Figure 3:
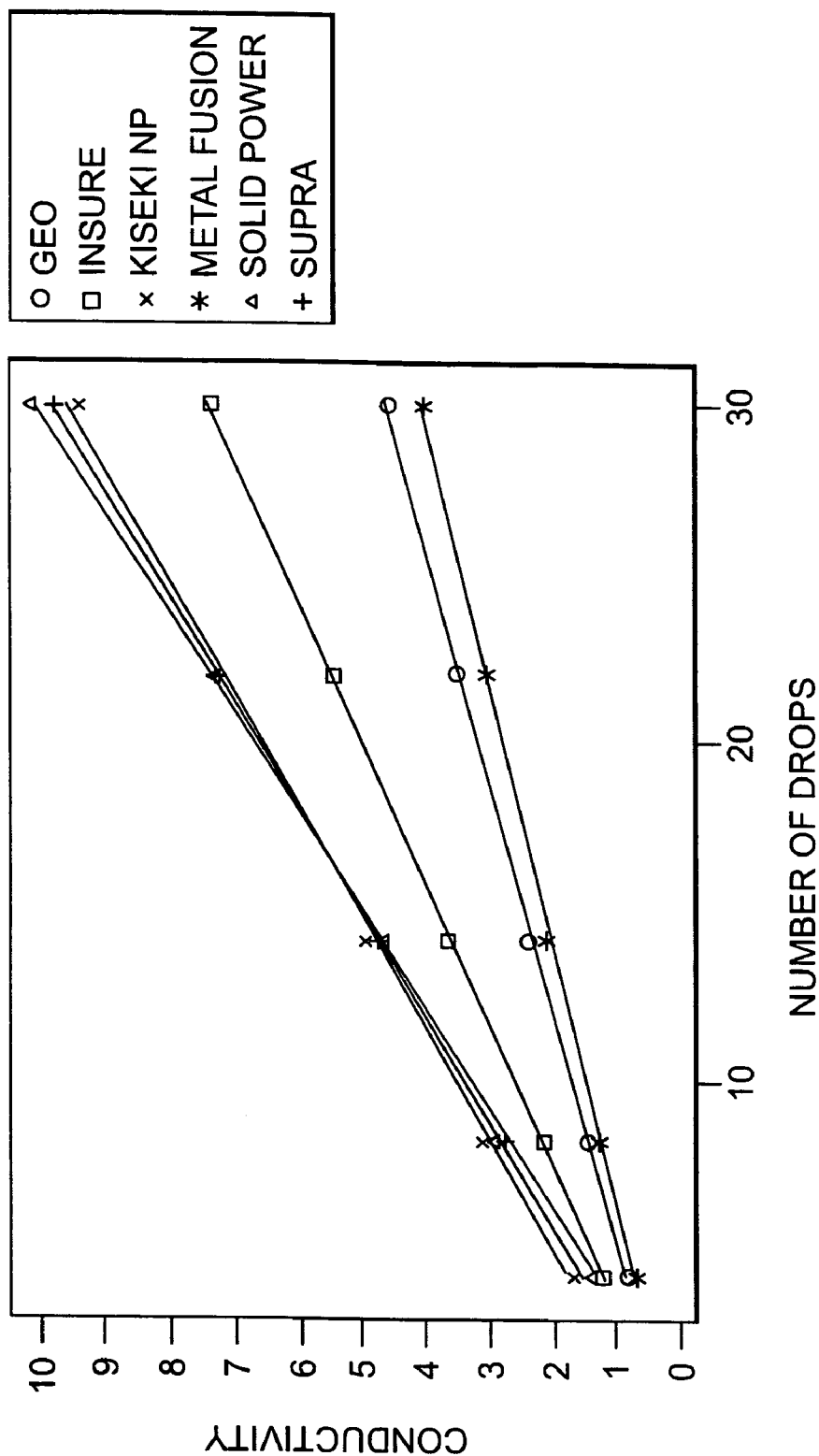
FIG. 3 is a chart similar to the chart of FIG. 2 but with measured conductivities made at the constant temperature of one hundred twenty degrees (120°) Fahrenheit.

The chart of FIG. 3 is similar to the chart of FIG. 2 but with measured conductivities made at the constant temperature of one hundred twenty degrees (120°) Fahrenheit. Again the conductivity curves for Geo Fusion and Metal Fusion have the lowest conductivities and again are very similar. Also again, the conductivity curves for Solid Power and Supra have the highest conductivities and again the curves are very similar. At this temperature, the conductivity curve for Kiseki NP approximates the conductivity curves for Power and Supra as well. And again, the conductivity curve for Insure is intermediate.

Figure 4:
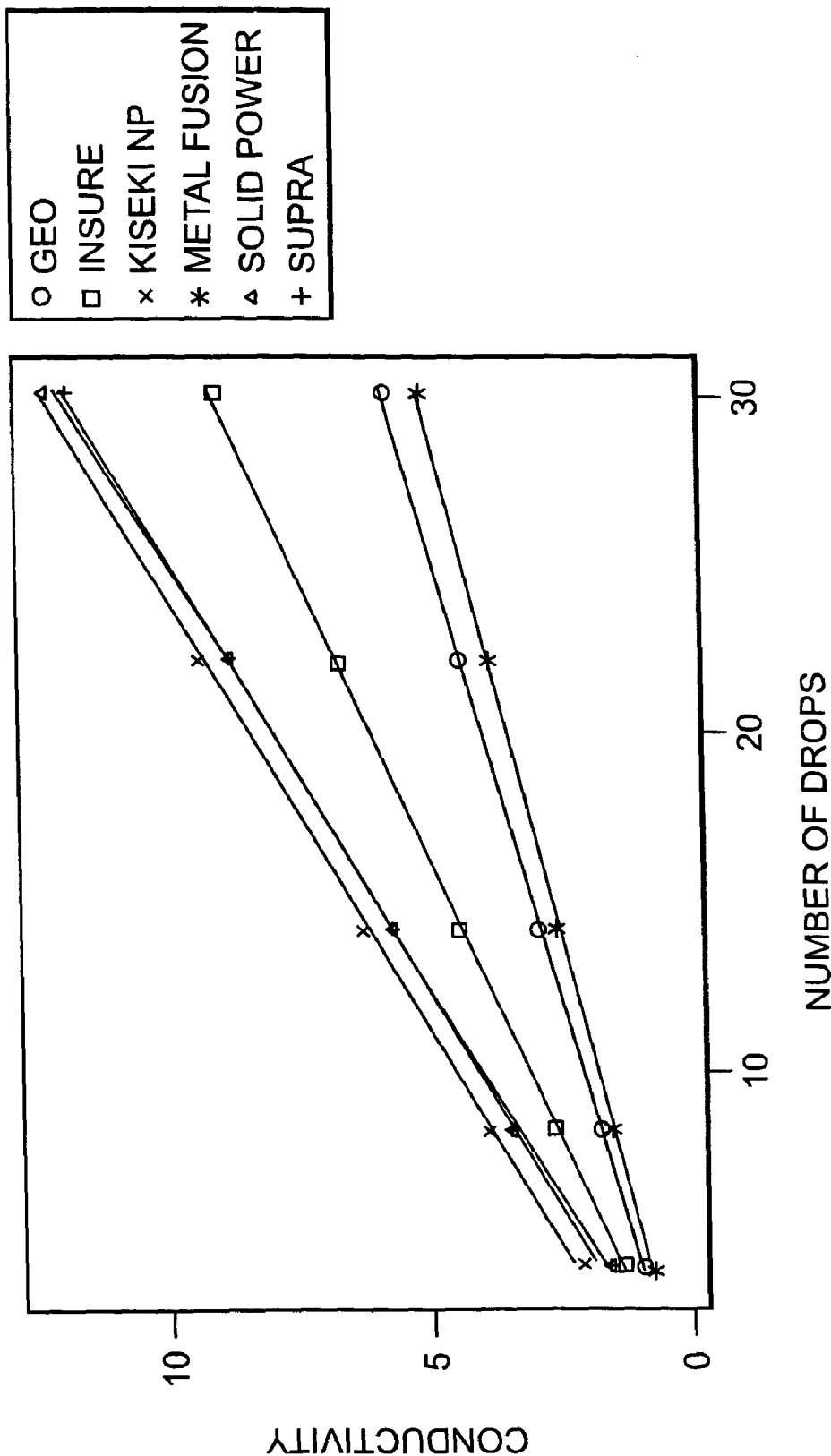
FIG. 4 is a chart similar to the charts of FIG. 2 and FIG. 3 but with measured conductivities made at the constant temperature of one hundred fifty degrees (150°) Fahrenheit.

The chart of FIG. 4 is similar to the charts of FIG. 2 and FIG. 3 but with measured conductivities made at the constant temperature of one hundred fifty degrees (150°) Fahrenheit. Although having steeper slopes, the conductivity curves for all concentrates are grouped similarly to the groupings identified in the chart of FIG. 3.

As noted in the empirical measurements indicated in the charts of FIGS. 1, 2, 3 and 4, the measured conductivity of a given concentrate increases as the temperature increases. Thus, while it is important to measure conductivity in order to determine the concentration of a given concentrate, an adjustment should also be made for temperature. Of course, one way to account for temperature change is to use a separate curve or a separate look-up table for each temperature. Another way to account for temperature change is to apply a correction factor. Conventional algorithms increase the conductivity by two percent (2%) for each one degree (1°) Centigrade rise in temperature. However, the table below shows that the six concentrates illustrated in FIGS. 1, 2, 3 and 4 actually have much different percentage correction factors when measured between twenty-five degrees (25°) and eighty-eight degrees (88°) Centigrade.

| | Calculated Correction Factor (25°-88° C.) | | | | | |
|---|---|---|---|---|---|---|
| Drops | Geo Fusion | Solid Power | Kiseki NP | Insure | Supra | Metal Fusion |
| 4 | 2.71 | 2.02 | 2.86 | 2.22 | 2.00 | 2.74 |
| 8 | 2.79 | 1.96 | 2.83 | 2.29 | 1.90 | 2.74 |
| 14 | 2.62 | 1.95 | 2.79 | 2.22 | 1.91 | 2.70 |
| 22 | 2.71 | 1.89 | 2.77 | 2.17 | 1.88 | 2.67 |
| 30 | 2.62 | 1.90 | 2.62 | 2.10 | 1.85 | 2.65 |
| Average | 2.69 | 1.94 | 2.78 | 2.20 | 1.91 | 2.70 |

Thus, it can be seen that measuring conductivity in order to determine concentration involves not only differing conductivities for a given amount of concentration but also involves differing temperature correction factors.

The measurements and results discussed above have been with respect to conductivity. References in this specification may also be made to resistivity. It is to be recognized and understood that conductivity and resistivity are related measurements with one being the inverse of the other. Thus, if the conductivity of a use solution is known, it is recognized and understood that the resistivity is also known simply by taking the inverse. And, of course, if the conductivity is known, it is recognized and understood that the resistivity is also, again by taking the inverse.

Figure 5:
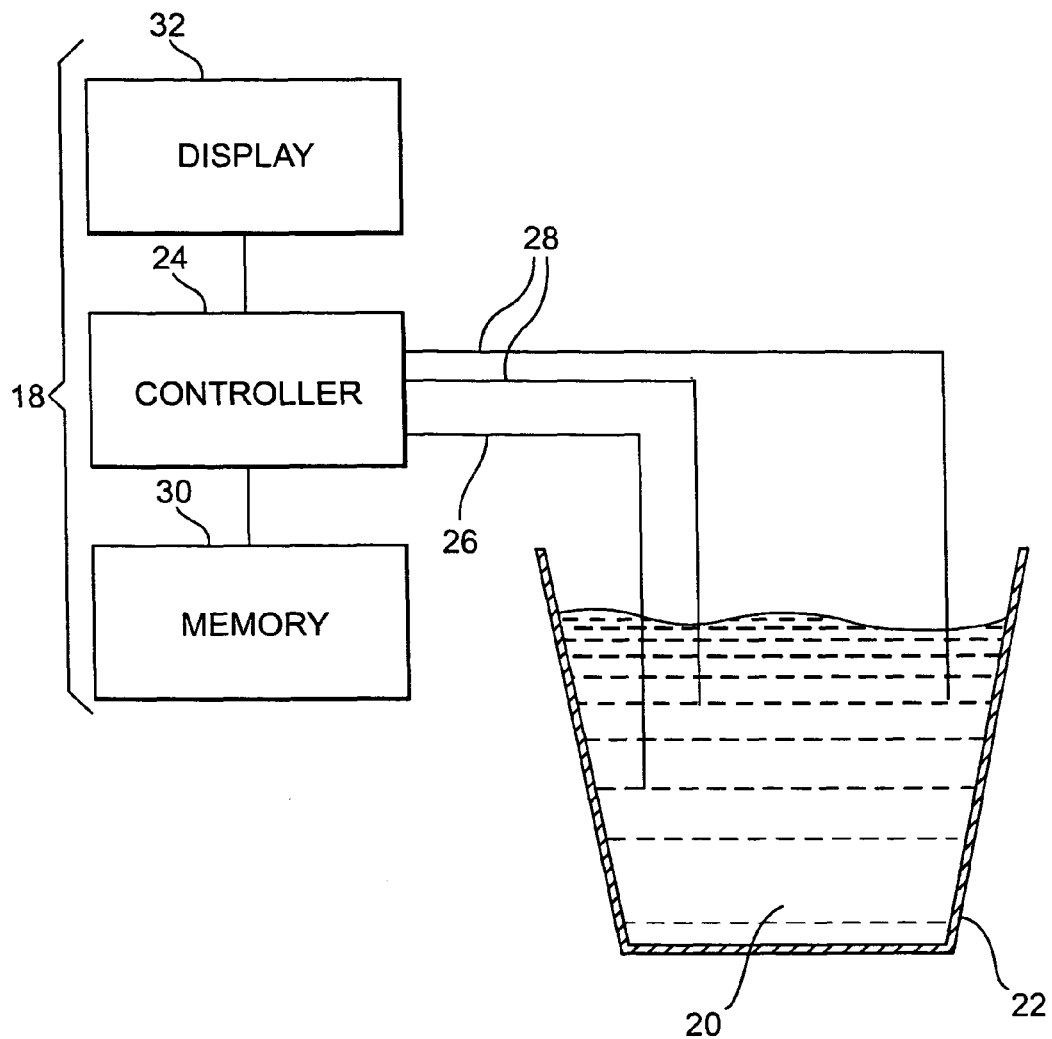
FIG. 5 shows an embodiment of a concentration monitor according to the present invention operatively coupled to a use solution.

FIG. 5 illustrates a concentration monitor 18 constructed and operating in accordance with the present invention. Concentration monitor 18 is shown operatively coupled to a liquid use solution 20 being held in container 22. Controller 24 is operatively coupled to use solution 20 with a conventional temperature probe 26 and a conventional conductivity probe 28. Temperature probe 26 can be any of a broad range of available commercial temperature probes. Conductivity probe 28 can also be any of a broad range of commercial conductivity probes including those discussed in relation to the empirical measurements discussed above.

Memory 30 is operatively coupled to controller 24. Memory 30 may store information needed by controller 24 to convert the information obtained by temperature probe 26 and conductivity probe 28 into a concentration. This information, preferably, has been obtained using the empirical measurements discussed above. Preferably, memory 30 may store the equation which has been fit to the empirical data. Alternatively, memory 30 may store a look up table which can be used by controller 24 for the conversion.

Memory 30 may also store the information needed by controller 24 to convert information obtained by temperature probe 26 and conductivity probe 28 into a concentration for a plurality of use solutions 20, i.e., a plurality of products contained in use solution 20, or a plurality of classes of products contained in use solution 20. A user of concentration monitor 18 may select information from memory 30 regarding at least one of the products, or classes of products, contained in the use solution 20 for use by controller 24.

If a first use solution 20, i.e., a use solution containing a first product or class of products, is to be monitored, concentration monitor 24 uses a first set of information from memory 30 to perform a determination of the actual concentration of use solution 20 using data obtained from temperature probe 26 and conductivity probe 28. When a different use solution 20, i.e., a use solution containing a second product or class of products, is to be monitored, concentration monitor 24 would then use a second set of information from memory 30 to perform a determination of the actual concentration of use solution 20 using data obtained from temperature probe 26 and conductivity probe 28. This enables concentration monitor 18 to effectively monitor the concentration level of a use solution 20 containing a first product, or first class of products, and, later, the concentration level of a use solution 20 containing a second product, or second class of products, using the same conductivity probe 28. The user of concentration monitor 18 need not switch conductivity probes (cells) 28 whenever a use solution 20 having a different product, or different class of products, is used.

Upon determining the actual concentration level of use solution 20, concentration monitor 18 may then display the results on display 32 such as by the display of a percentage concentration level or an alarm signal if the concentration falls below a predetermined threshold, for example. The user may then take appropriate action, such as replenishing the supply of concentrate in use solution 20.

Figure 6:
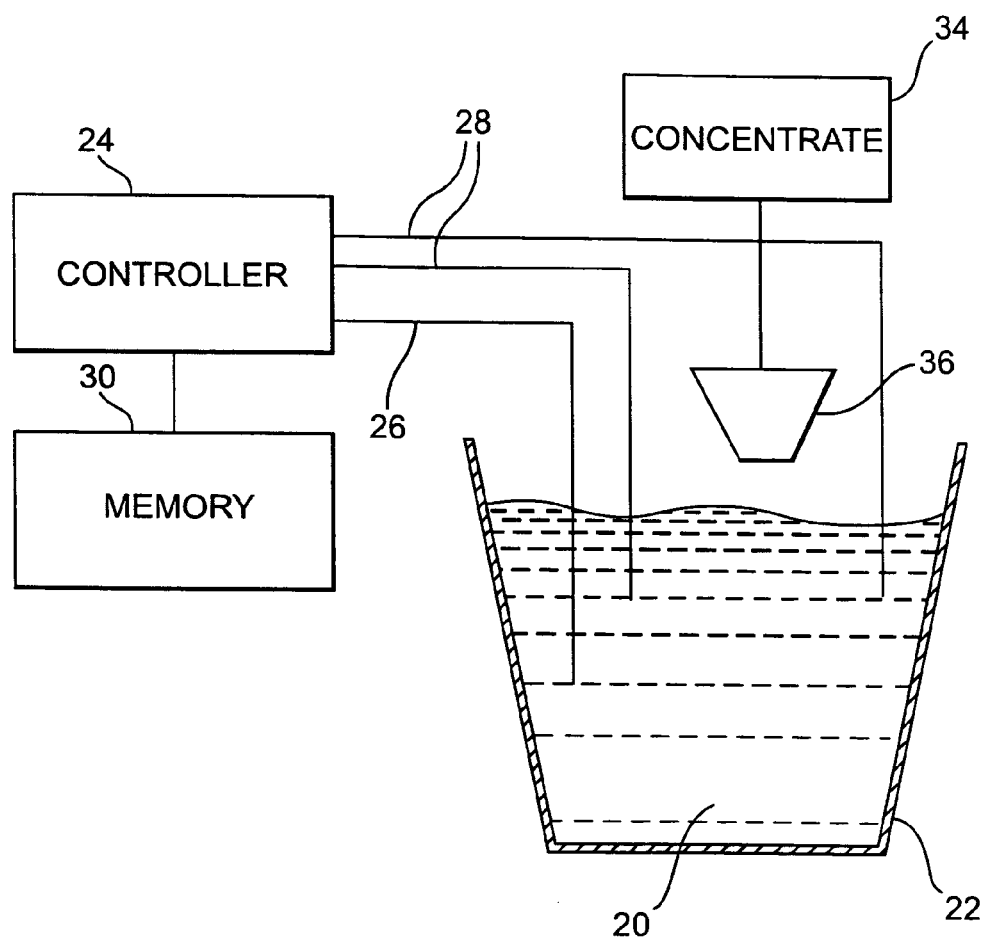
FIG. 6 shows an alternative embodiment of a concentration monitor according to the present invention adapted to automatically add concentrate to a use solution upon the concentration reaching a predetermined threshold.

In an alternative embodiment illustrated in FIG. 6, concentration monitor 18 having controller 24 and memory 30 is operatively coupled to use solution 20 in container 22 with temperature probe 26 and conductivity probe 28, similar to concentration monitor 18 of FIG. 2. The algorithm for determining the concentration level selection from memory 30 occurs in the same way. The temperature of use solution 20 is measured with temperature probe 26 in the same way. The conductivity of use solution 20 is measured with conductivity probe 28 in the same way. The concentration is calculated by controller 24 in the same way. Concentration monitor 18 illustrated in FIG. 3 determines when the concentration of concentrate 34 reaches a predetermined level. However, instead of displaying the results of the concentration, or displaying an alert, for example, to a user, concentration monitor 18 actually adds concentrate 34 through hopper 36 to increase the concentration of concentrate 34 in use solution 20 to an acceptable level. Thus, concentration monitor 18 illustrated in FIG. 3 not only monitors and measures the concentration level of use solution 20 but also automatically replenishes the supply of concentrate 34 in use solution 20. In this way, the proper concentration level of concentrate 34 in use solution 20 is maintained.

In a preferred embodiment, a user of concentration monitor 18 could select an algorithm, or look up table, from memory 30 from eight settings based on product classification. The desired equation or look up table would be used to determine the concentration of use solution 20 and, hence, control the addition of concentrate to use solution 20.

As an example for use solutions based on detergents, one controller algorithm could be used for a class of extruded products having naturally relatively low conductivity. Another setting could be used for very high concentrations of highly conductive liquid or solid caustic for applications found, for example, in food and beverage and vehicle care use situations.

Figure 7:
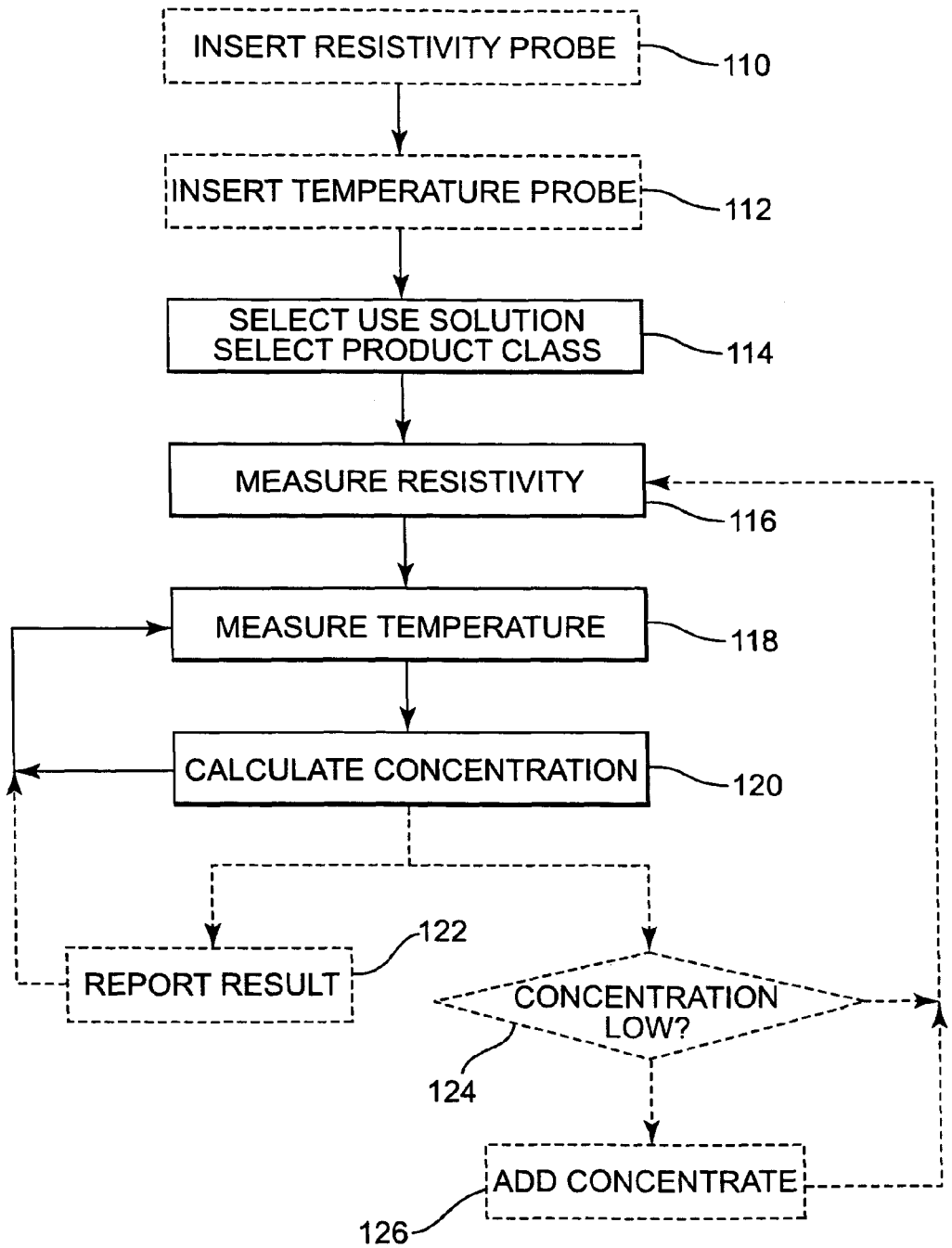
FIG. 7 shows a flow diagram of an embodiment a method in accordance with an embodiment of the present invention.

FIG. 7 is a flow chart illustrating a technique for calculating concentration using the measurements and calculations described above. The method starts in block 110 with the optional step of inserting a resistivity (or conductivity) probe into the use solution being measured. In the optional step identified in block 112, a temperature probe is inserted into the same use solution. Steps 110 and 112 are optional because the method of the present invention may be employed in an environment where resistivity (or conductivity) and temperatures probes have already been inserted into the use solution. This would be the case, for example, in an existing installation where the method of the present invention is utilized to upgrade an existing prior art concentration monitor.

The particular use solution being measured is selected (block 114). Of course, the selection of step 114 could be made before, during or after steps 110 and 112.

The conductivity of use solution 20 is read (step 116) as an analog voltage. The analog voltage is converted from an analog voltage to conductivity value in milliSiemens per square centimeter (mS/cm$^2$) using a known equation or predetermined look up table. The temperature of use solution 20 is read (step 118) also as an analog voltage. The analog voltage is then converted to a temperature value in degrees Celsius using a known equation or a predetermined look up table. Of course, the measuring of steps 116 and 118 could occur in either order or, preferably, occur simultaneously.

Once the particular use solution 20 has been selected and the resistivity (or conductivity) and temperature have been measured, then the concentration of the concentrate in the particular use solution 20 can be calculated (block 120) using the techniques discussed above. The method can then repeat by returning to steps 116 and 118 to continue measuring resistivity (or conductivity) and temperature.

Optionally, the concentration determined in step 120 can be reported (block 122) to a user such as by a conventional display, signal, alarm or other communication technique. The method can then repeat by returning to steps 116 and 118 to continue measuring resistivity (or conductivity) and temperature.

Alternatively and, again, optionally, the concentration determined in step 120 can be compared with a predetermined standard to determine if the concentration of use solution 20 is too low (block 124). If the concentration is at or below the predetermined standard, then additional concentrate 34 can be added (block 126) to use solution 20. Whether or not the concentration is too low and whether or not concentrate 34 is added, the method can then return to steps 116 and 118 to continue measuring resistivity (or conductivity) and temperature.

Various modifications and alterations of this invention will be apparent to those skilled in the art without departing from the scope and spirit of this invention. It should be understood that this invention is not limited to the illustrative embodiments set forth above.

What is claimed is:

1. A concentration monitor comprising:
   a resistivity probe that measures resistivity of a selected one of a plurality of use solutions;
   a temperature sensor that measures a temperature of the selected use solution;
   a memory that stores a plurality of predetermined algorithms, each associated with a different one of a plurality of product classifications; and
   a controller that calculates a concentration of a product in the selected use solution based on the resistivity, the temperature and one of the plurality of the predetermined algorithms associated with a product classification of the product in the selected use solution.

2. The concentration monitor of claim 1 wherein the controller stores information concerning identification of the selected use solution.

3. The concentration monitor of claim 2 wherein the controller receives user selected information concerning identification of the selected use solution a user controllable setting.

4. The concentration monitor of claim 1, further including a user interface that reports the concentration to a user.

5. The concentration monitor of claim 1 wherein the algorithm is linear.

6. The concentration monitor of claim 1 wherein the controller performs a function based upon the concentration.

7. The concentration monitor of claim 1 wherein the controller further controls addition of concentrate of the product to the use solution when the concentration falls below a predetermined level.

8. The concentration monitor of claim 1 wherein the algorithm is determined based on empirical measurements of use solutions having known product concentrations.

9. The concentration monitor of claim 1 wherein the algorithm is determined based on empirical measurements of the conductivity of use solutions having known product concentrations.

10. The concentration monitor of claim 8 wherein the empirical measurements are taken over a range of temperatures.

11. The concentration monitor of claim 8 wherein the algorithm includes an equation fit to the empirical measurements.

12. The concentration monitor of claim 8 wherein the algorithm includes a lookup table corresponding to the empirical measurements.

13. The concentration monitor of claim 1 wherein the product classification is user selectable.

* * * * *